United States Patent [19]

Wheeler et al.

[11] Patent Number: 5,362,508
[45] Date of Patent: Nov. 8, 1994

[54] PROCESS FOR PREPARING SOFT CENTERS IN FOOD PRODUCTS

[75] Inventors: Edward L. Wheeler, Fairfield; G. Curtis Busk, Jr., Chester, both of N.J.

[73] Assignee: Nabisco, Inc., Parsippany, N.J.

[21] Appl. No.: 924,724

[22] Filed: Aug. 3, 1992

Related U.S. Application Data

[63] Continuation-in-part of Ser. No. 804,140, Dec. 6, 1991, Pat. No. 5,258,197, which is a continuation-in-part of Ser. No. 624,056, Dec. 7, 1990, abandoned, which is a continuation-in-part of Ser. No. 410,161, Sep. 20, 1989, abandoned.

[51] Int. Cl.$^5$ ............................................. A23D 7/00
[52] U.S. Cl. ................................ 426/302; 426/306; 426/502; 426/607; 426/549; 426/98; 426/99
[58] Field of Search ............... 426/560, 99, 517, 502, 426/98, 302, 306, 607, 549

[56] References Cited

U.S. PATENT DOCUMENTS

| | | |
|---|---|---|
| 1,437,816 | 12/1922 | Paine et al. |
| 3,496,886 | 2/1970 | Fohr . |
| 3,574,639 | 4/1971 | Forkner ................................ 426/99 |
| 3,666,388 | 1/1972 | Oberwelland et al. . |
| 4,150,163 | 4/1979 | Peterson . |
| 4,229,484 | 10/1980 | Steels et al. . |
| 4,260,596 | 4/1981 | Mackles . |
| 4,296,135 | 10/1981 | Rutten ................................ 426/517 |
| 4,360,534 | 11/1982 | Brabbs . |
| 4,514,430 | 4/1985 | Hartman . |
| 4,517,205 | 5/1985 | Aldrich . |
| 4,584,203 | 4/1986 | Du Vall ............................... 426/502 |
| 4,596,714 | 6/1986 | Brabbs . |
| 4,722,849 | 2/1988 | Dartey . |
| 4,840,803 | 6/1989 | Polizzano . |
| 4,894,246 | 1/1990 | Dartey . |
| 4,938,128 | 7/1990 | Knebl . |
| 4,961,941 | 10/1990 | Cocco ................................ 426/560 |
| 4,961,942 | 10/1990 | Cocco ................................ 426/560 |
| 4,965,076 | 10/1990 | Martin ............................... 426/560 |
| 4,965,077 | 10/1990 | Martin ............................... 426/560 |
| 5,023,099 | 6/1991 | Boehm .............................. 426/560 |
| 5,035,905 | 7/1991 | Knebl . |
| 5,180,603 | 1/1993 | Moriya .............................. 426/502 |
| 5,223,292 | 6/1993 | Thulin .............................. 426/502 |
| 5,258,197 | 11/1993 | Wheeler ............................ 426/607 |

OTHER PUBLICATIONS

Patton 1976 Biomedical Aspects of Lactation Pergamon Press New York p. 82.

Shishikura 1986 Agric. Biol Chem 50(5) 1209–1215.

*Primary Examiner*—Carolyn Paden

[57] ABSTRACT

Food products having soft or liquid centers, layers or other areas are formulated by arranging two fat-containing components contiguous with one another. A fat in the first component migrates into the second, forming a mixture having a lower solids content than the second fat, while the structural integrity of the first component is maintained. The process is especially adapted to the formation of soft- and liquid-centered confections. One preferred embodiment employs fats bearing long, saturated $C_{16}$ to $C_{22}$ fatty acid residues and a mixture of short $C_2$ to $C_4$ acid residues, preferably containing acetic acid residues, as the migrating fat in a confectionery coating, and hydrogenated coconut or palm kernel oil as the fat in the confectionery center. An especially preferred embodiment employs, as the migrating fat, triglycerides bearing long, saturated substitutents containing at least about 75% stearic acid residues and short residues derived from acetic acid, a mixture of acetic and propionic acid, or a mixture of acetic and butyric acid. Since sucrose and invertase are not essential elements of the center, artificial sweeteners can be used to replace all or part of the sucrose, resulting in reduced calorie confections. Caloric reduction is further enhanced because preferred migrating fats are low in calories.

25 Claims, 1 Drawing Sheet

PROCESS FOR PREPARING SOFT CENTERS IN FOOD PRODUCTS

RELATED U.S. APPLICATION DATA

This is a continuation-in-part of co-pending U.S. application Ser. No. 804,140, filed Dec. 6, 1991, now U.S. Pat. No. 5,258,197 hereby incorporated in its entirety by reference, which was a continuation-in-part of U.S. application Ser. No. 07/624,056, filed Dec. 7, 1990, now abandoned, which was a continuation-in-part of U.S. application Ser. No. 07/410,161, filed on Sep. 20, 1989, now abandoned.

TECHNICAL ART

This invention relates to a process for making soft and liquid centers in food products such as confections.

The manufacture of food products having contrasting textures is generally achieved by using expensive, specialized equipment or incorporating additives into food product components. Dual textured confectionery products, for example, are commonly prepared by making a shell and then filling it. Alternatively, invertase can be added to the ingredients of a candy center to soften it over time, but the technique involves the use of an additive and sugar is required as a substrate for the enzyme's activity.

It would be desirable to have other methods of softening portions of food products that do not involve additives or special equipment.

BACKGROUND ART

The classical method for making soft- or liquid-centered food products, notably candies such as chocolate-covered cherries, employs invertase as an ingredient in a sugar fondant center (U.S. Pat. No. 1,437,816 to Paine and Hamilton). During manufacture, the sugar fondant center is firm and easily enrobed with chocolate or another coating; on storage, the enzyme slowly hydrolyzes sucrose to invert sugar. The invert sugar is more soluble than sucrose in the moisture of the fondant, so it melts under the coating, converting the firm center into a creamy liquid. The process requires sucrose as the enzyme substrate, however, and so is unsuitable for centers containing other sweeteners.

Other methods require specialized, mechanically intricate equipment and/or multistep manufacturing processes involving shell formation and filling. For example, in U.S. Pat. No. 3,666,388 to Oberwelland and Klahn, hollow sweetmeats are made by spinning an open top mold containing a measured quantity of castable confectionery material and cooling the body until it forms a shell, which is subsequently filled. U.S. Pat. No. 4,260,596 to Mackles discloses an analogous method for preparing a hard outer shell covering by chilling a molten mannitol composition in a hemisphere mold until a sufficiently thick wall has been formed; the shells are then filled.

U.S. Pat. No. 3,496,886 to Fohr discloses a process involving the cooling of a liquid filling to a temperature below the sugar saturation temperature before casting the rapidly cooled filling liquid into molds to form a candy unit with a hard crust. U.S. Pat. No. 4,517,205 to Aldrich discloses codeposition of a two-component hard candy wherein the components have specified sugar contents and specific gravities. U.S. Pat. No. 4,229,484 to Steels and Dacey discloses a method of making center-filled bars of chocolate by depositing shell forming and filling materials into molds from a depositor comprising, for example, two separated and independently heated hoppers by means of pairs of independently operated plungers. Other apparatuses have been designed to fashion fold-over soft center-filled confections (U.S. Pat. No. 5,035,905 to Knebl) and soft-centered ropes (U.S. Pat. No. 4,938,128 to Knebl).

It would be desirable to provide a process for making filled and layered multi-textured food products that does not involve food additives or specialized equipment. It would also be desirable to provide a process for making soft- and liquid-centered confections that do not have sucrose as the exclusive sweetener in the center.

DISCLOSURE OF THE INVENTION

An object of the present invention is to provide a process for making food products having regions of contrasting textures such as soft- and liquid-centered food products.

It is another object of the invention to provide a process for preparing soft centers in food products that does not require additives or special equipment.

It is a further object of the invention to provide a process for preparing soft- and liquid-centered confections having centers that contain little or no sucrose.

These and other objects are accomplished by the present invention, which provides a process for preparing a food product containing regions of contrasting textures comprising layering a fat-containing composition and then coating the layer with another composition containing a fat that migrates into the layer at equilibrium under conditions effective to soften the layer. The fat component in the coating is selected so that it migrates into the layer and the fat component in the layer is selected to have a solids content that decreases upon mixture with the migrating fat. Very little migration occurs in the opposite direction, so the fat layer from which migration occurs remains hard.

In preferred embodiments, soft- or liquid-center food products are formed by layering a center with a fat that migrates into the center, softening it. For example, firm fondants prepared with coconut or palm kernel fats enrobed with a coating composition containing short-/long triglycerides bearing long $C_{16}$ to $C_{22}$ saturated fatty acid residues and $C_2$ to $C_4$, preferably $C_2$ to $C_3$, short acid residues soften appreciably as the short/long triglycerides migrate into the coconut or palm kernel fat, yet the coating remains firm.

GENERAL DESCRIPTION OF THE INVENTION

Figure 1:
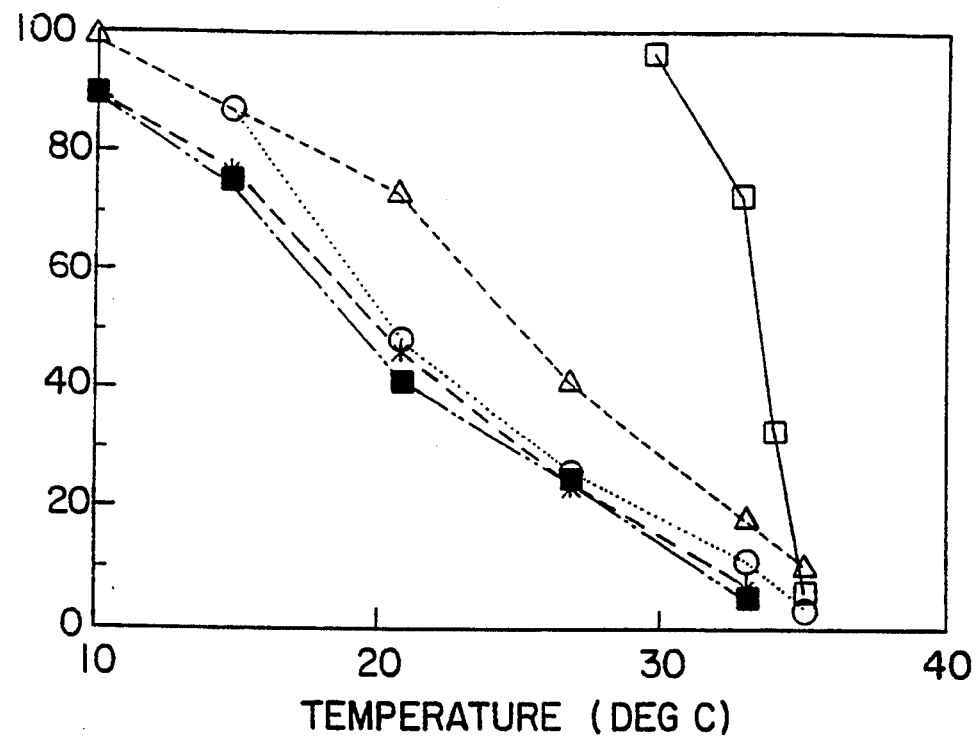
FIG. 1 illustrates how solids in a coconut fat candy change over time when held in proximity to a cream filling containing diacetostearin. Differential scanning calorimetry (DSC) is employed to determine solid fat profiles; diacetostearin at time zero is denoted —☐—. The coconut coating fat at time zero is denoted -- ▷ --; after five days, the solids profile changes (·· ⊙ ··). This effect nearly reaches equilibrium after (- - ✳ - -), with little change observed after at 6 weeks (—■—).

Food products containing regions of contrasting textures are formulated according to this invention by employing at least two fat-containing components contiguous with one another. The fats in the components are selected so that one fat migrates into the other, forming a eutectic mixture that has a lower solids content than the original fat. In preferred embodiments, a firm fat-containing center is coated with a composition containing a fat that migrates into the center, softening it.

Food component compositions enriched with triglycerides bearing both long, saturated $C_{16}$ to $C_{22}$ fatty acid residues and short $C_2$ to $C_4$ acid residues, notably $C_2$ to $C_3$ acid residues, are particularly useful as the migrating fat. In a preferred embodiment, the long fatty acid residues are predominantly, i.e., at least about 75% and, in some embodiments at least about 90%, $C_{18}$, and the short acid residues are acetic acid or a mixture of acetic and propionic acid residues.

Denoting the aliphatic portion of the long fatty acid substituent as L and the short as S, a migrating fat of this invention comprises a mixture of SSL, SLS, LLS, and LSL species described by the following formulae:

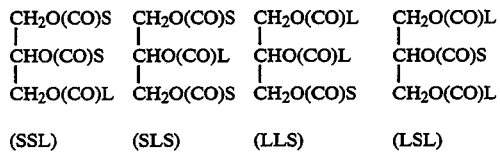

where
  each L, independently, is a long chain saturated aliphatic group having between 15 and 21 carbons, derived from a fatty acid having 16 and 22 carbons; and
  each S, independently, is a short chain group having 1 to 3 carbons, derived from an acid having 2 to 4 carbons.

In preferred embodiments, the migrating fat has S groups derived from acetic acid, but may also contain some propionic acid or butyric acid or a mixture of these, and at least about 85%, more preferably at least about 90%, of the fat mixture comprises SSL/SLS species.

Depending upon the preparative procedure, the triglyceride mixtures may also contain triglycerides of the formulae

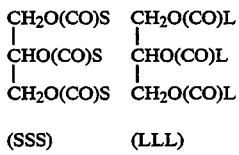

where S and L are as defined above. However, preferred mixtures contain essentially no SSS and less than 2% LLL.

Short acid residues have 2 to 4 carbons. Short residues are derived from carboxylic acids of the formula SCOOH, where S is a short chain aliphatic group having 1 to 3 carbons. As denoted herein, where triglycerides are described as bearing pendant groups derived from acids having 2, 3, or 4 carbons, compositions derived from acids having predominantly 2, 3, or 4 carbons are included. Acylation of a glycerol hydroxyl by acid SCOOH results in the attachment of short chain S to the glycerol backbone by means of an ester linkage (—O—(CO)—). Where there is more than one short group attached to a glyceride, the groups may be the same or different. As used herein, the term "acid residue" refers to an acyl group comprising a short chain portion, here S, and a carbonyl group.

Short chain S may be straight or branched. Short chain S may be derived from any synthetic or natural organic acid including, but not limited to acetic (ethanoic), propionic (propanoic), butyric (butanoic), and the like acids. As used herein, chemical names include isomeric variations; for example, "butyric acid" includes normal-butyric acid (butanoic) and iso-butyric (2-methylpropanoic) acid, and so forth. Preferred acids are acetic, propionic, butyric and mixtures of these. Especially preferred are S complements containing acetic acid.

The long saturated pendant groups are derived from fatty acids of the formula LCOOH, where L is a saturated aliphatic group having 15 to 21 carbons. L groups may be derived from any synthetic or natural, straight or branched saturated organic acid including, but not limited to, palmitic (hexadecanoic), stearic (octadecanoic), arachidic (eicosanoic), behenic (docosanoic), and the like acids.

Unsaturated long groups may also be present in the mixtures. These are derived from unsaturated acids of the formula UCOOH, where U is a $C_{15}$ to $C_{19}$ unsaturated group, including, but not limited to, palmitoleic (9-hexadecenoic), oleic (cis-9-octadecenoic), elaidic (trans9-octadecenoic), vaccenic (trans-11-octadecenoic), linoleic (cis, cis-9,12-octadecedienoic), linolenic (9,12,15-octa-decatrinoic and 6,9,12-octadecatrienoic), eleostearic (9,11,13-octadecatrienoic), arachidonic (5,8,11,14-eicosatetraenoic), and the like acids. L groups may be derived from hydrogenated U groups.

The various L and U groups can be derived from mixtures of fatty acids obtained from natural oils such as soybean, safflower, sunflower, sesame, peanut, corn, olive, rice bran, mustard seed, cottonseed, poppyseed, rapeseed, marine, meadowfoam and the like oils; fats such as babassu nut oil, palm oil, palm kernel oil, tallow, lard, shea butter, dairy butter; or plant waxes such as jojoba. Fat mixtures and/or fractions, crystallized fats, interesterified fats and mixtures of these may also be employed.

Mixtures of L groups are preferably derived from oils and fats that are hydrogenated, most preferably fully hydrogenated. Hydrogenated fats having at least about 70%, preferably at least about 75%, stearic acid residues such as, for example, hydrogenated peanut oil, hydrogenated olive oil, hydrogenated soybean oil, hydrogenated sesame oil, and hydrogenated corn oil are especially desirable for some embodiments. Other embodiments employ L moieties derived from hydrogenated fats having at least about 90% stearic acid residues, such as hydrogenated sunflower oil, hydrogenated safflower oil and hydrogenated canola. Preferred hydrogenated feedstocks are low in palmitic acid.

Component triglycerides making up the migrating fats of this invention may be prepared using synthetic procedures known to those skilled in the art, such as, for example, directly esterifying glycerol or glycerol esters with fatty acids, fatty acid halides (notably chlorides) or fatty acid anhydrides, transesterifying glycerol with fatty acid esters, or interesterifying long and short chain triglycerides for such time and under such conditions that triglycerides bearing long and short residues form. Starting materials for triglyceride preparations may be obtained commercially or isolated from natural sources. Alternatively, component triglycerides may be isolated from natural or processed fats or oils, or fractions thereof.

Some desirable migrating triglyceride mixtures are prepared by reacting monostearin with acetic anhydride; inclusion of about 5 to 10% propionic or butyric anhydride or a mixture of these is preferred. Alternatively, triacetin can be randomly interesterified with a substantially hydrogenated fat having at least about 70%, in some cases at least about 75%, and, in some embodiments, at least about 90%, stearic acid residues such as hydrogenated canola; inclusion of about 5 to 10% tripropionin or tributyrin in the initial reaction mixtures is preferred. Mixtures and fractions of triglycerides may also be employed, such as mixtures of products derived by interesterifying triacetin with hydrogenated hydrogenated soybean oil and mixing this with acetylated monostearin. Example preparations are illustrated hereafter.

Isolated or prepared migrating triglycerides are purified using techniques known to those skilled in the art. These include, but are not limited to, steam deodorization, fractional crystallization, distillation, chromatography, and the like. Example purifications are illustrated hereafter.

Migrating fats are used in a portion of a food product that is in contact with another portion containing a fat that has a solids content that decreases upon mixture with the migrating fat. Any fat that forms a mixture having lower solids can be used; fats that form eutectic mixtures are especially preferred. Example fats may include hydrogenated corn, soybean, safflower, sunflower, sesame, peanut, and the like oils, and dairy and cocoa butter. Especially preferred with the above described preferred short/long migrating fats are hydrogenated coconut and palm kernel oils.

BEST MODES FOR CARRYING OUT THE INVENTION

In the practice of this invention, a fat-containing portion of a food product is softened by the migration of another fat from a second, contiguous portion. The migrating fat forms a mixture having a lower solids content than the fat originally in the portion. In preferred processes, a center or core portion containing a firm fat such as hydrogenated coconut or palm kernel oil is coated with a composition containing a fat that, upon equilibrating, migrates into the center portion and softens it. Yet the coating composition retains its structural integrity because little migration occurs in the opposite direction.

The process of this invention can be employed in the manufacture of any food product having fat-containing portions in contact with each other, such as, for example, candies, bakery products such as pastries, cookies and crackers, dessert products, snack products, and dairy products. For cookies, chocolate or other fat-containing chips can be incorporated into the dough in their typical hard form and then softened over time in accord with the invention by migration of fat from the cookie into the chip. Judicious selection of a fat that migrates and a fat having a solids content that decreases upon mixture with the migrating fat can be applied to soften centers, layers, and specific areas of the products to achieve the texture, taste, and appearance desired in the final product.

The process of this invention is especially adapted to the manufacture of soft- and liquid-centered confections, especially chocolates having a cream filling. As used herein, a "cream filling" includes any filling having a fat component, whether or not the filling has the actual consistency of a cream. Cream fillings typically have a fat component making up about 25 weight percent to about 35 weight percent of the total filling composition. The fillings may additionally have an aqueous component of water, milk, fruit juice or other liquid. The process of this invention is applicable to low density fillings containing up to about 22% water such as candy foams and gummy candies, medium density fillings containing about 5 to about 15% of an aqueous phase such as chewy candies, and high density fillings containing little or no aqueous phase. Preferred fillings are formulated with hydrogenated coconut oil or hydrogenated palm kernel oil.

Preferred migrating fats are the short/long triglycerides described above. These may be incorporated either alone, or in combination with another fat and/or fat mimetic. Other fats include butter, cocoa butter, natural triglycerides rich in highly desirable or essential fatty acids, such as oleic, linoleic, linolenic, or eicosapentaenoic acid, triglycerides bearing fatty acids having beneficial attributes such as those associated with conjugated linoleic acid isomers, medium chain triglycerides and the like. Other fat mimetics include any heretofore suggested as edible fat replacements, including, but not limited to, sugar esters, neoalkyl esters, polyglycerol esters, malonate esters, propoxylated glycerols, retrofats, carboxy/carboxylates, polyvinyl alcohol esters and the like.

When employed either alone or in products with other fats, short/long triglycerides are desirably added to a portion of a food product in amounts effective to soften another contiguous portion of the product. For example, a 25% or greater replacement of the usual fat component can be effective for this purpose, and replacements of at least 50% are desired in many cases. As a chocolate coating on a confectionery, preferred embodiments employ short/long triglycerides in full replacement of the coating fat component. Preferred chocolate embodiments employ cocoa powder or other chocolate flavoring rather than cocoa butter.

Confectionery cream centers made according to the process of this invention ordinarily contain a sweetener and a flavoring in addition to the fat component. The sweetener can be a natural sweetener such as sugar, primarily sucrose, glucose, fructose, and maltose, honey, or any one of known artificial sweeteners including 1-aspartyl-1-phenylalanine methyl ester (commercially available as aspartame or Nutri-Sweet TM), saccharine, cyclamate and the potassium salt of 6-methyl-3,4-dihydro-1,2,3-oxathiazin-4-one-2,2dioxide (commercially available as acesulfame-K), or a mixture of these. Reduced calorie confections prepared using the process of this invention employ little or no sucrose.

Cream center compositions made using to the process of this invention can also contain other ingredients depending upon the flavor or other properties desired. For instance, milk or milk powders or solids (preferably nonfat) can be included, as can eggs, gelatin, cornstarch or other starch such as potato or rice, fruits and nuts, molasses, colorings, and lecithin or other emulsifiers. Compositions containing artificial sweeteners substantially sweeter than sucrose typically contain a bulking agent such as polydextrose, isomalt, isomaltulose, polyglucose, polymaltose, carboxymethyl-cellulose, microcrystalline cellulose, cellulose gel, arabinogalactan, as well as mixtures or combinations of any of these. These agents can be included in amounts readily determinable by the skilled artisan.

For soft- and liquid-centered confections, cream fillings are formulated using a fat in the fat component that has a solids profile that decreases upon the addition of the migrating fat. The fat component and other ingredients are mixed, and, optionally aerated, before enrobing with a composition containing the migrating fat using means familiar to the skilled artisan. The confections may, optionally, be enrobed or glazed with other layers. The confections are then allowed to equilibrate for a time under conditions that result in fat migration from the coating and formation of a mixture having a lower solids content in the center portion. This is generally accomplished merely by storing the product at room temperature for one to three weeks; specific examples are illustrated hereafter.

An important advantage of the present invention is that contrasting textures can be achieved in food products without the use of additives. In the manufacture of soft- or liquid-centered confections, for example, adding invertase is unnecessary. Centers or layers containing sweeteners other than sucrose that would be impervious to the action of invertase can be readily softened using the process. In the manufacture of confectioneries, fondant centers hard enough to enrobe easily can be softened on storage for only a short time.

Another advantage is that soft centers or layers in food products can be achieved without special equipment or multistage processes involving shell formation followed by filling. This is achieved simply by selecting a coating fat that will migrate into a center or layer fat, with little migration in the other direction.

Another advantage of the present invention is that softening can be modulated by judicious selection of the amount and kind of fats in the different food product portions. A very soft filling, for example, is produced when diacetostearin or acetopropionylstearin is employed as the sole migrating fat with hydrogenated coconut or palm kernel oil as the sole filling fat. A considerably firmer filling is produced when the same migrating fat is employed with a soybean oil-based filling fat. The effect can be varied by further manipulating the amount and type of the fats in the components.

Where the process of this invention is employed using preferred migrating fats in chocolate confections, another advantage is that these fats have a unique crystal structure, and they do not require tempering. Some can even be quench cooled. This greatly simplifies the overall candy manufacturing process.

Products made with the process of this invention exhibit a number of desirable characteristics. Preferred migrating fats of the invention are low in calories, so that foods prepared according to the process of this invention are reduced calorie products. Moreover, since sucrose is not required as a substrate for invertase, soft- and liquid-center confections can be formulated using low calorie sweeteners, enhancing the decrease in the caloric content of the product.

Where preferred migrating fats are employed in chocolate-like coatings, the confections exhibit minimal or no bloom. As is familiar to the skilled artisan, "bloom" is a separation of fat crystals from the matrix of a chocolate coating, generally caused by separation of cocoa butter from the matrix and extrusion or recrystallization of fat to or on the surface with the consequent formation of a white layer or splotches. Bloom is usually ascribed to partial liquefication (due, for instance, to temperature fluctuations) and then recrystallization of the fat which sometimes migrates to the surface. Although tempering, the formation of stable crystals via a commonly used cooling and slow heating process, can help in retarding bloom, bloom remains a recurring problem in the chocolate confection industry.

Another advantage of the invention is that employment of preferred short/long triglycerides as the migrating fats provides a wide range of densities and textures in the products. Since many coatings incorporating these fats are quick-setting, less cooling is required, simplifying production. Moreover, products containing these as coating fats can be stored on the shelf and/or at higher temperatures than controls.

EXAMPLES

The following examples are presented to further illustrate and explain the present invention and should not be taken as limiting in any regard. Unless otherwise indicated, all parts and percentages are by weight, and are based on the weight at the particular stage of the processing being described. Solid fat indices (herein abbreviated S.F.I.) are determined using dilatometry according to A.O.C.S. Method Cd 10-57 (1989), reporting solids at 50° F. (10° C.), 70° F. (21.1° C.), 80° F. (26.7° C.), 92° F. (33.3° C.), and 100° F. (37.8° C.). Mettler dropping points (M.D.P.) are determined using a Mettler Thermosystem FP 800 following A.O.C.S. Method Cc 18-80 (1989).

NMR data reported are proton NMR data. NMR S/L ratios are determined as the ratio of intensities of the methyl (—$CH_3$) resonances for the short and long fatty acid groups, respectively, obtained by dividing the integral areas attributable to S components by the areas attributable to the L, and have experimental errors of about 5 to 10%. In a typical NMR spectrum at 300 MegaHertz or higher, the long acid methyl resonance occurs farthest upfield, at ~0.9 ppm, as a triplet. The short acid methyl resonance is structure dependent and occurs at ~2.00 ppm (acetyl groups), ~1.15 ppm (propionyl groups) and ~0.95 ppm (butyryl groups).

Fat product analysis using supercritical fluid chromatography (S.F.C.), separating and quantifying fat mixture components and the extent of fat migration, generally employ a standard procedure. After filtering through a 0.45 micron filter, 0.1 ul of a 30 to 50 mg/ml sample is injected onto a 1×100 mm Deltabond Cyano ™ column from Keystone Scientific in a Suprex Model 200A S.F.C. having an S.F.C.-grade carbon dioxide mobile phase and an oven temperature of 115° to 125° C. A linear pressure gradient of 100 to 300 atmospheres is applied over a course of 20 minutes (i.e., 10 atm/min), followed by a hold at 300 atmospheres for 10 minutes. A flame ionization detector at 375° to 400° C. detects emerging mixture components run against an internal standard of methyl tetradecanoate (10 to 12 mg/mL) in methylene chloride. External standards (~10 mg/mL each) are run under identical conditions. Using these peak areas, the peak areas of the sample are normalized, added together, and divided by the total to obtain percentages of species in the mixtures.

Differential scanning calorimetry (DSC) is used to obtain information about the melting and crystallization behavior of the facts and solids content at any given temperature. A sample is cooled from about 20° C. above its melting point to about 20° C. below, held at the final temperature, and then reheated to the initial temperature. Crystallization and melting thermograms are subjected to several analyses. The melting point(s) are taken as the peak minima (endothermic transition in the down direction of the chart plotting mW per unit time versus temperature) obtained in the heating cycle, and the crystallization temperature as the peak onset in the cooling cycle. Enthalpies of phase transitions are automatically calculated in mJoules/mg of sample by choosing the two temperature points of onset of melting and 100% melted. Percent solids, i.e., the percent liquid portion of the sample at any given temperature, are calculated by integration.

Example 1

In this example, migrating fats for use in making chocolate confections having liquid centers are prepared.

Fat product A, diacetostearin (diacetyl stearoyl glyceride), is prepared by reacting monostearin with acetic anhydride. A 2-L, 3-neck flask equipped with a stirrer, heating mantle, thermometer, and reflux condenser is charged with 406 g monostearin obtained from Spectrum Chemicals (~97% pure). This is melted prior to addition of acetic anhydride (~98% pure, obtained from Aldrich Chemicals), and the mixture is refluxed at 140° C. for 2 hours, held overnight without heat, and refluxed for 3 more hours. Acetic acid is distilled off, and the product purified in a falling-film still (1 mm Hg, 180° C.) to yield 438 g (83%) of a golden yellow solid. NMR shows that the product contains triglycerides only, which have a fatty acid profile of 66% acetic acid and 34% stearic acid residues.

Another fat mixture, denoted B, is prepared by randomly interesterifying 1 molar equivalent hydrogenated canola (899 g of a refined, low erucic rapeseed oil containing 4% palmitic acid, hydrogenated at 180° C. and 60 lbs hydrogen until the Iodine Value (IV) is ≦3), 11 molar equivalent of triacetin, and 1 molar equivalent of tripropionin by heating the reactants in the presence of 0.2 to 0.3% sodium methoxide to ~110° C. with agitation under a vacuum for about half an hour until color develops. (The M.D.P. may be checked at this time, and the reaction continued if the M.D.P. has not dropped sufficiently.) Phosphoric acid (~0.2 to ~0.5%, at least twice the amount of sodium methoxide) is added to stop each reaction and neutralize the mixture, followed by the addition of 0.5% activated bleaching clay (Tonsil Optimum FF), 0.5% diatomaceous earth, and 1000 ppm citric acid (dissolved in water) to decolorize and remove soaps. The treatment is continued for ½ to 1 hour at 110° C. The product is cooled to 80° C., filtered, bleached, and steam deodorized at 210° C. for 2 to 3 hours.

Using this procedure, fat product B having a M.D.P. of 35° C. and exhibiting an S.F.I. of 64.4% at 50° F., 62.4% at 70° F., 58.7% at 80° F., 28.5% at 92° F., and 0.4% at 100° F. is obtained. S.F.C. species analysis shows 83.7% SSL/SLS, 15.4% SLL/LSL, and 0.9% LLL. The NMR fatty acid profile shows 51% acetic, 13% propionic, and 36% long acid residues; the S/L ratio is 1/8.

Fat product B is further characterized using standard fat research methodology. The smoke point is 260° F., the flash point, 470° F. and the fire point, 495° F. using A.O.C.S. Method Cc 9a-48. The congeal point is 33.8° C. using A.O.C.S. Method Cc 14-59; the saponification value is 347 using A.O.C.S. Method Cd 3-25; the AOM oxidative stability is 290+hours using A.O.C.S. Cd 12-27; the peroxide value is 0.45 meq/kg using A.O.C.S. Method Cd 8-53; free fatty acids are 0.78% using A.O.C.S. Method Ca 5a-40; the specific gravity is 0.9337 @ 60° using Cc 10-25; the refractive index is 1.4385 @ 60° C. using A.O.C.S. Method Cc 7-25; and the Lovibond color is 20 Red/77 Yellow using A.O.C.S. Method Cc 13b-45.

A third migrating fat product C is prepared by reacting a 1:1.5:0.5 reactant molar ratio of monostearin:acetic:propionic acid. Three hundred g (0.84 moles) glycerol monostearin obtained from Spectrum Chemicals (~97%, lot # EF027) are reacted with 54.7 g (0.42 moles) propionic anhydride (Aldrich Chemicals) and 128.6 g (1.26 moles) acetic anhydride (~99%, Aldrich Chemicals) as set out for the preparation of diacetostearin described above. The product is purified through a falling film still and deodorized for 2 hours at 180° C. (<1 mm Hg, 40 mls H₂O) to produce 318.7 g of a soft waxy golden solid having a capillary melting point of 30–32° C. Proton NMR analysis shows a triglyceride content of 91%, with 36% stearic acid, 23% propionic and 42% acetic acid residues. S.F.C. analysis shows 67.9% acetic and 32.1% propionic acid in the SSL/SLS component.

Example 2

This example illustrates how fat migration causes softening of one part of a confectionery.

A chocolate bar is prepared using 92° hydrogenated coconut oil obtained from Vandenberg Foods (IV≦5%). This is layered to a depth of 1 centimeter with a cream fondant prepared by blending 50% sugar with 50% diacetostearin fat product A of Example 1. The DSC melting profile is followed with time for both the cream and the chocolate stored at room temperature.

The results are plotted in FIG. 1. The coconut candy fat (- -△- -) is softer than the diacetostearin cream (—☐—) at the outset, but still hard to the touch, goes from approximately 75% solids at room temperature to about 45% ( ·⊙· ·) after only five days of storage in contact with the cream. The chocolate is soft and gooey. This effect nearly reaches equilibrium after 3 weeks (- - * - -), with little change observed after at 6 weeks (—■—).

Figure 2:
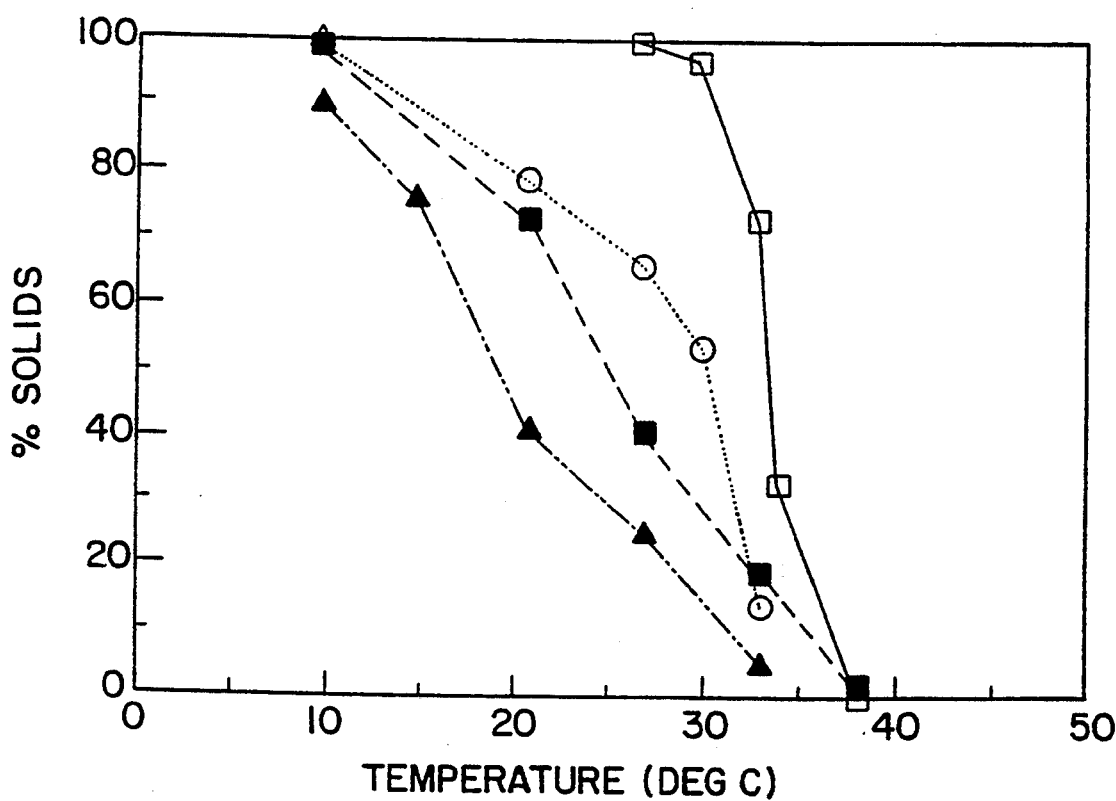
FIG. 2 shows that, in the experiment referred to in FIG. 1 above, the solids profile of the diacetostearin (fresh control, —☐—) also changes (6 weeks contact, ·· ⊙ ··) when held in proximity to the coconut fat (fresh control, —■—; 6 weeks contact, —▶—).

The diacetostearin cream also softens (from —☐—to ···⊙·· after 6 weeks; see FIG. 2). Its mouthfeel becomes softer than the rather hard feel of the freshly prepared cream fondant, but it does not become soft and gooey, nor does it melt in the hand.

Example 3

This example quantifies the migration of fats between the coating and center of a chocolate bonbon.

Chocolate bonbons are prepared by mixing 50% sugar with 50% fat product B of Example 1, and coating this cream with the hydrogenated coconut oil chocolate described in Example 2. These are compared with control bonbons prepared by coating a cream containing a commercial soybean oil product coated with the same chocolate.

After storage, the confections having centers containing product B soften considerably and become gooey and messy, while the control candies do not.

Samples of the cream fillings and the coatings are analyzed using S.F.C. after storage together at ambient temperature, and the results are compared with values obtained using the fats before storage. In addition to some migration from the coating into the cream filling, the resulting chromatograms show a significant migration of diacetostearin from the cream filling into the coating, along with some minor SSL/SLS components containing propionic acid residues. The LLS/LSL components do not migrate. After six weeks contact, the coconut based coating has become approximately 25% diacetostearin. The control filling fat does not migrate into the same coating.

Example 4

A chocolate candy is prepared by combining equal parts confectioner's sugar, cocoa powder, and fat product B prepared in Example 1 above, mixing thoroughly at 55° to 65° C. with 0.5% by weight lecithin. The mixture is then poured into molds and allowed to cool to ambient temperature or refrigerated.

Following the procedure of Example 2 above, this chocolate is stored in direct contact with Akapol E ™, a commercially available chocolate product containing hydrogenated soybean oil. The Akapol ™ softened, but to a lesser extent than that observed with the coconut fat product of Example 2.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims.

We claim:

1. A process for preparing a food product containing regions of contrasting textures comprising formulating a first fat-containing composition and then coating the composition with a second composition containing a different fat comprising at least 25% a mixture of triglycerides bearing both long, saturated $C_{16}$ to $C_{22}$ fatty acid residues and short $C_2$ to $C_4$ acid residues that migrates into the fat in the first composition upon equilibrating, under conditions effective to soften the first composition while retaining the structural integrity of the second composition.

2. A process according to claim 1 wherein the fat in the first composition comprises hydrogenated coconut or palm kernel oil.

3. A process according to claim 1 wherein the short residues are derived from acids selected from the group consisting of acetic acid, mixtures of acetic and propionic acid, and mixtures of acetic and butyric acid.

4. A process according to claim 3 wherein at least about 75% of the long acid residues are stearic acid residues.

5. A process according to claim 4 wherein the short acid residues are a mixture of acetic and propionic acid residues.

6. A confectionery product having a center softened using the process of claim 1.

7. A method for softening the fat-containing center of a confectionery product comprising coating the center with a composition containing a fat comprising at least 25% a mixture of triglycerides bearing both long, saturated $C_{16}$ to $C_{22}$ fatty acid residues and short $C_2$ to $C_4$ acid residues that, upon incubation for a time and under conditions that result in the migration of the fat into the center, forming a fat mixture in the center having a fat solids content lower than the original fat in the center.

8. A method according to claim 7 wherein the fat in the center is selected from the group consisting of hydrogenated coconut oil and hydrogenated palm kernel oil.

9. A method according to claim 7 wherein at least about 75% of the long, saturated fatty acid residues are stearic acid residues and the short acid residues are derived from acids selected from the group consisting of acetic acid, mixtures of acetic and propionic acid, mixtures of acetic and butyric acid, and mixtures thereof.

10. A method according to claim 9 wherein the triglycerides are described by the formulae

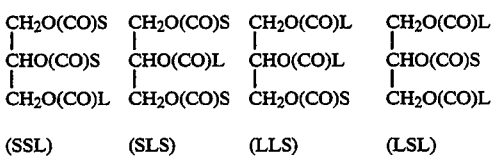

where
each L, independently, is a long chain saturated aliphatic group having between 15 and 21 carbons, derived from a fatty acid having 16 and 22 carbons; and
each S, independently, is a short chain group having 1 to 2 carbons, derived from an acid having 2 to 4 carbons,
and at least about 85% of the mixture comprise SSL and SLS species.

11. A method according to claim 10 wherein at least about 90% of the mixture comprise SSL and SLS species.

12. A method according to claim 8 wherein the migrating fat comprises diacetostearin.

13. A confectionery product made according to the method of claim 7 wherein the center contains little or no sucrose.

14. A chocolate confectionery product made according to the method of claim 10.

15. In a process for preparing a soft-centered confectionery product comprising preparing a center with a composition containing sucrose and invertase, enrobing the center with a coating composition, and incubating for a time under conditions that the sucrose acts as a substrate for the invertase, an improvement wherein said center is prepared with a fat component comprising hydrogenated coconut or palm kernel oil and without invertase and is enrobed with a coating composition containing another fat comprising at least 25% a mixture of triglycerides bearing both long, saturated $C_{16}$ to $C_{22}$ fatty acid residues and short $C_2$ to $C_4$ acid residues that migrates into the center fat component, resulting, upon incubation, in a fat mixture in the center having a lower fat solids content.

16. An improvement according to claim 15 wherein the center contains little or no sucrose.

17. An improvement according to claim 15 wherein said coating composition is a chocolate coating composition.

18. An improvement according to claim 15 wherein the triglycerides in the coating composition bear short acid residues derived from acids selected from the group consisting of acetic acid, a mixture of acetic acid and propionic acid, a mixture of acetic acid and butyric acid, and a mixture of acetic acid, propionic acid, and butyric acid.

19. An improvement according to claim 18 wherein the triglycerides in the coating composition fat bear short acid residues derived from a mixture of acetic acid and propionic acid.

20. An improvement according to claims 19 wherein the triglycerides in the coating composition fat bear short acid residues derived from a mixture of acetic acid and butyric acid.

21. A method for softening the cream center of a confectionery product enrobed with a firmer fat-containing coating composition comprising: formulating the center with hydrogenated coconut or palm kernel oil or a mixture of these; and formulating the fat component of the coating composition with at least 25% triglycerides bearing both long, saturated $C_{16}$ to $C_{22}$ fatty acid residues containing at least about 75% stearic acid residues and short acid residues derived from acids selected from the group consisting of acetic acid, mixtures of acetic acid and propionic acid, mixtures of acetic acid and butyric acid, and mixtures thereof, so that the coating fat component migrates into the center fat component, resulting in a fat mixture in the center having a lower fat solids content while the structural integrity of the coating composition is maintained.

22. A method according to claim 21 wherein the center of the confectionery product contains no sucrose.

23. A method according to claim 21 for softening the fat-containing center of a confectionery product enrobed with a chocolate coating comprising formulating the center with hydrogenated coconut or palm kernel oil or a mixture of these, and formulating at least 25% of the coating fat component with a mixture of triglycerides of the formulae

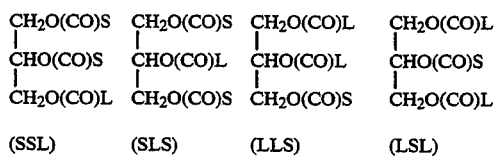

where
each L, independently, is a long chain saturated aliphatic group having between 15 and 21 carbons, derived from a fatty acid having 16 and 22 carbons, provided that at least about 75% are derived from stearic acid, and each S, independently, is a short chain group having 1 to 3 carbons, derived from an acid having 2 to 4 carbons, provided that at least a portion of the S residues are acetic acid residues, and also provided that at least 85% of the mixture comprise SSL and SLS species, wherein the coating fat component migrates into the center fat component, resulting in a fat mixture in the center having a lower fat solids content while retaining the structural integrity of the coating.

24. A method according to claim 23 wherein the S groups are derived from acids selected from the group consisting of a mixture of acetic and propionic acid.

25. A method according to claim 23 wherein the S groups are derived from acids selected from the group consisting of a mixture of acetic and butyric acid.

* * * * *